United States Patent
Duggal et al.

(10) Patent No.: US 8,992,568 B2
(45) Date of Patent: Mar. 31, 2015

(54) SYSTEMS AND METHODS FOR CEREBROSPINAL FLUID REPAIR

(75) Inventors: Neil Duggal, London (CA); Louise C. Raymond, London (CA); Joshua A. Butters, Chandler, AZ (US)

(73) Assignee: Neil Duggal, London, Ontario (CA)

( * ) Notice: Subject to any disclaimer, the term of this patent is extended or adjusted under 35 U.S.C. 154(b) by 933 days.

(21) Appl. No.: 12/582,250

(22) Filed: Oct. 20, 2009

(65) Prior Publication Data

US 2010/0100107 A1 Apr. 22, 2010

Related U.S. Application Data

(60) Provisional application No. 61/106,675, filed on Oct. 20, 2008, provisional application No. 61/172,852, filed on Apr. 27, 2009.

(51) Int. Cl.
*A61B 17/08* (2006.01)
*A61B 17/12* (2006.01)
*A61B 17/00* (2006.01)

(52) U.S. Cl.
CPC ..... *A61B 17/12022* (2013.01); *A61B 17/12109* (2013.01); *A61B 17/12113* (2013.01); *A61B 17/12136* (2013.01); *A61B 17/12172* (2013.01); *A61B 17/12186* (2013.01); *A61B 17/00491* (2013.01); *A61B 2017/1205* (2013.01)
USPC .......................................... 606/213; 606/215

(58) Field of Classification Search
USPC ......... 606/213, 215, 139, 144, 151, 157, 200, 606/216, 219; 604/103.12, 103.09
See application file for complete search history.

(56) References Cited

U.S. PATENT DOCUMENTS

| | | | | |
|---|---|---|---|---|
| 3,874,388 | A | * | 4/1975 | King et al. .................... 606/232 |
| 4,327,736 | A | * | 5/1982 | Inoue ....................... 604/101.05 |
| 4,655,745 | A | | 4/1987 | Corbett |
| 5,976,174 | A | * | 11/1999 | Ruiz ............................. 606/213 |
| 6,743,200 | B2 | | 6/2004 | Sachs |
| 6,899,726 | B2 | | 5/2005 | Sachs |
| 7,150,737 | B2 | | 12/2006 | Pham |
| 7,238,364 | B2 | | 7/2007 | Swhney |
| 2001/0000797 | A1 | | 5/2001 | Mazzocchi |
| 2004/0034321 | A1 | | 2/2004 | Robinson |
| 2004/0049154 | A1 | | 3/2004 | Larnard |
| 2004/0167468 | A1 | | 8/2004 | Larnard |
| 2005/0049634 | A1 | | 3/2005 | Chopra |
| 2005/0149158 | A1 | | 7/2005 | Maiti |
| 2005/0288706 | A1 | * | 12/2005 | Widomski et al. ............ 606/213 |
| 2007/0093860 | A1 | | 4/2007 | Rao |

(Continued)

*Primary Examiner* — Gregory Anderson
(74) *Attorney, Agent, or Firm* — Maywood IP Law; Barbara Daniels; David Meibos

(57) ABSTRACT

A system and method for treating a defect. The system may comprise a first expandable barrier insertable into a defect interior space in a compact state and then expanded once positioned inside the defect. The first expandable barrier is expanded to be positioned against the inner surface of the defect. The system may also comprise a second barrier which may be expandable, positioned against the outer surface of the defect. Each of the first and second barriers may expand laterally to a greater extent than axially. The first and second barriers may be in communication through a connection member which couples the two barriers together. The barriers each obliterate the defect and can prevent subsequent CSF or other fluid leaks. Fibrin glue may be introduced into the defect to seal and secure the barriers to the defect. Each barrier may comprise a mesh, a basket, an umbrella or a balloon.

14 Claims, 27 Drawing Sheets

(56) References Cited

U.S. PATENT DOCUMENTS

| | | |
|---|---|---|
| 2007/0179527 A1* | 8/2007 | Eskuri et al. .................. 606/213 |
| 2007/0276340 A1 | 11/2007 | Brady |
| 2008/0065150 A1 | 3/2008 | Drasler |
| 2008/0146990 A1 | 6/2008 | Drasler |
| 2008/0208268 A1 | 8/2008 | Kruth |
| 2008/0228200 A1 | 9/2008 | Baird |
| 2009/0112273 A1 | 4/2009 | Wingeier |
| 2009/0112277 A1 | 4/2009 | Wingeier |
| 2009/0112278 A1 | 4/2009 | Wingeier |
| 2009/0112279 A1 | 4/2009 | Wingeier |
| 2009/0112280 A1 | 4/2009 | Wingeier |

* cited by examiner

US 8,992,568 B2

SYSTEMS AND METHODS FOR CEREBROSPINAL FLUID REPAIR

CROSS-REFERENCE TO RELATED APPLICATIONS

This application claims the benefit of:

U.S. Provisional Patent Application No. 61/106,675, filed 20 Oct. 2008, and is entitled CEREBROSPINAL FLUID REPAIR DEVICE; and U.S. Provisional Patent Application No. 61/172,852, filed 27 Apr. 2009, and is entitled CEREBROSPINAL FLUID REPAIR DEVICE.

The above-identified documents are incorporated herein by reference.

BACKGROUND OF THE INVENTION

1. The Field of the Invention

The present invention relates generally to the repair of cerebrospinal fluid leaks and reconstruction of anatomy from defects, and more particularly, from leaks which may result from a region of incompetence in the dura mater or cranial vault.

2. The Relevant Technology

Recent advances in endoscopic sinus surgery as well as traditional skull base approaches have produced an increasing number of CSF leaks following surgery. Acute or chronic CSF leaks have significant associated morbidity, including meningitis, pneumocephalus, intracranial hypotension, brain abscesses and seizures. More and more oncologic skull base surgeries are performed via a transnasal endoscopic approach, resulting in significant rate of CSF leaks. In addition, unintentional craniofacial trauma and transcranial skull base surgery can result in CSF leaks. Finally, in select patients, no identifiable etiology is found (idiopathic).

Traditionally, transcranial approaches were used to repair CSF leaks. This approached involved a craniotomy, brain retraction, and dural patch and some type of fibrin seal. More recently, in an attempt to limit morbidity, transnasal endoscopic techniques have been successful in repairing select skull base CSF fistulas. During an endoscopic repair, either abdominal fat or fascia lata from the thigh are most commonly used as grafting material to occlude the dural defect. Other materials include, pericardium, mucoperichondrium, middle turbinate bone as well as a variety of vascularized mucoperiosteal flaps. These materials are used for obliteration, an overlay graft or an underlay graft. Obliteration of the sphenoid sinus can be performed with any of the listed grafting materials. In an underlay technique, the grafting material is inserted a few millimeters intradural between the dura and the bone on all sides of the defect. Less successful is the overlay technique, where the grafting material is simply placed over the dural or bone defect and secured typically with fibrin glue. In conjunction, a variety of materials are used in conjunction with the grafting material and include fibrin glue, an absorbable gelatin sponge (Gelfoam) and an absorbable knitted fabric (Surgicel). In addition, a lumbar drain is typically inserted and kept in place to divert CSF for 3-7 days, depending on the The techniques described above, for repair of CSF leaks, can be unreliable, require a second incision to harvest grafting material and commonly necessitate the use of a lumbar drain. Lumbar drains are typically used for 3-7 days and inserted at a distant site (lumbar) through a separate stab incision. They may be highly problematic, requiring frequent position changes of the catheter. There may also be at high risk of dislodgement and unintentional removal. When a patient has a lumbar drain in place, frequent monitor of the neurological status is required from the nursing staff. This may significantly increase the length and cost of the hospital stay following endoscopic surgery and is associated with potential complications including headaches, meningitis, intracranial hypotension, chronic CSF leaks and spinal abscess. Patients poorly tolerate this invasive post-operative procedure for CSF diversion.

As the above described techniques illustrate, the existing systems and procedures for repairing CSF leaks may not be as effective as desired.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for reconstruction and repair of defects resulting in cerebrospinal fluid (CSF) leak. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

One embodiment of the present invention includes a repair device. The repair device includes a first barrier, a second barrier and a connecting member that couples the first and second barriers together. The material of the first and second barriers may be soft and malleable so as to prevent injury to adjacent structures. The first barrier may comprise the connecting member or it may be a separate component. The first barrier may be positioned on one side of the defect with a first inserter tube and then the first barrier expanded, creating a first seal against a first surface of the defect or surrounding structure. Such expansion of the first barrier can be accomplished through many different means, for example, the use of a gas or a liquid for inflation or the use of mesh or a reinforcing body that is configured to expand laterally when manipulated. The second barrier may be positioned on the opposite side of the defect with a second inserter tube, the second barrier creating a second seal against a second surface of the defect, surrounding structure, or the first barrier itself. The first barrier, which may be an inlay, and the second barrier, which may be an overlay, are connected via a connection member. The barriers may be secured, covering the defect, in a number of ways such as by suturing, nailing, riveting, adhering, or stapling techniques. A sealing material such as fibrin glue may also assist in sealing or fixing the device in place with respect the defect or the device itself.

Figure 1A:
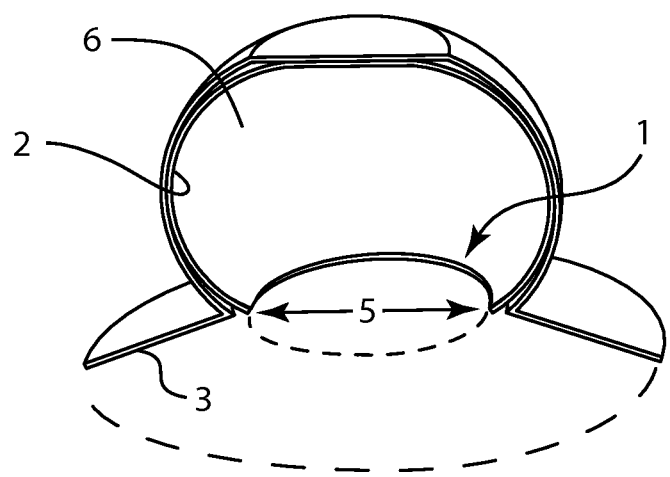
FIG. 1A is a stylized cross-sectional view of a defect having an inner surface, an outer surface, and a lateral dimension.

Referring to FIG. 1A, a stylized defect is shown. Defect opening 1 is an opening between an inner surface 2 and an outer surface 3. The defect has a lateral dimension 5, which is the widest dimension of the defect opening 1 between the inner 2 and outer 3 surfaces. A defect interior space 6 is distal to the defect opening 1 and generally surrounded by inner surface 2. In one example of a sella defect, a defect in the dura and bony tissues comprising the sella may be formed when a pituitary tumor is removed endoscopically via the nasal cavity. In this example, the inner surface 2 is the dura mater, and the outer surface 3 is the thin bony tissues of the sella floor.

Figure 1B:
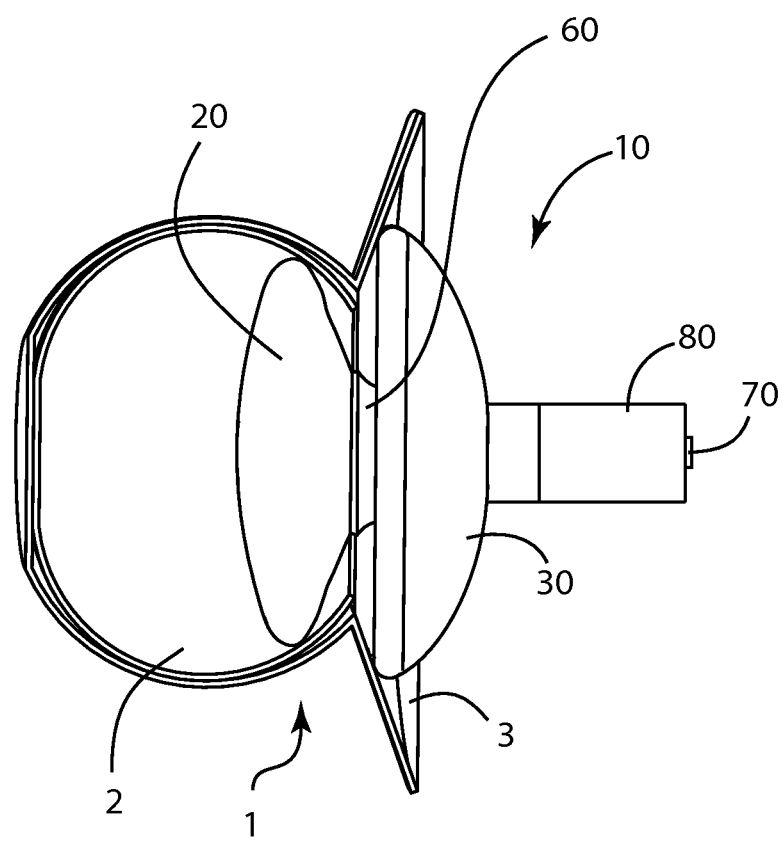
FIG. 1B illustrates a side view of a defect in cross section and a defect repair device having an inlay, an overlay, a seal, an inlay inserter tube and an overlay inserter.
Figure 2:
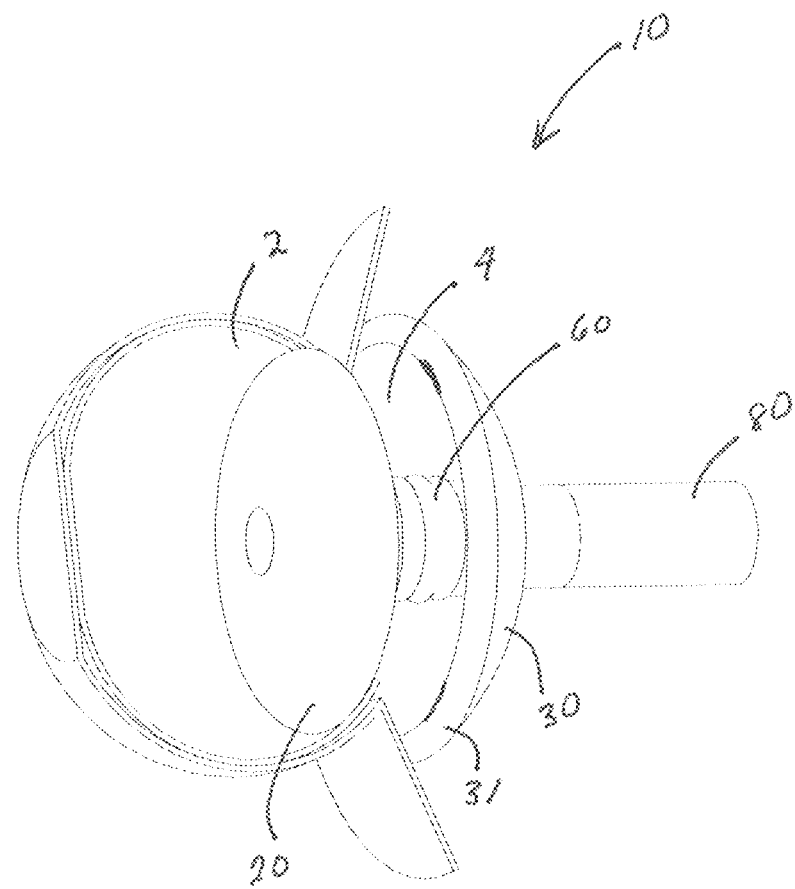
FIG. 2 illustrates a perspective top view of the defect repair device of FIG. 1 from a distal vantage point with the defect in cross section, the inlay, the overlay, the seal and the overlay inserter tube.
Figure 3:
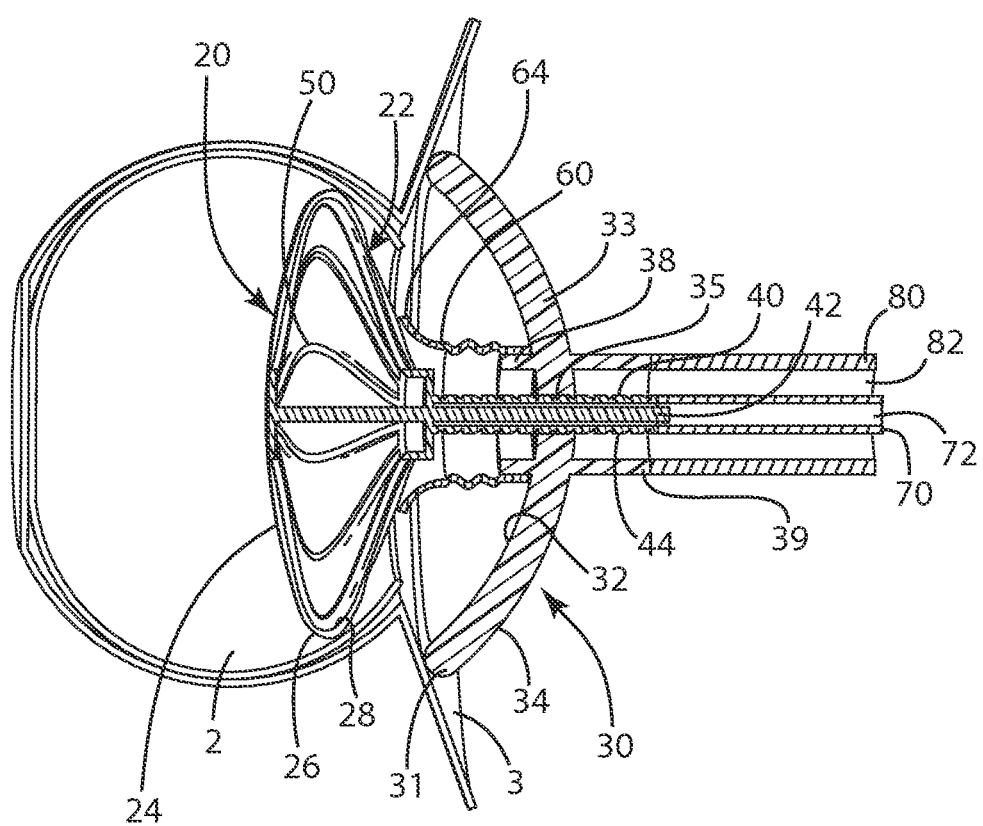
FIG. 3 illustrates a cross sectional side view of the defect repair device of FIG. 1 with an inlay with a reinforcing body, a connecting member with a hollow bore, an inlay inserter tube with a hollow bore, and an overlay inserter tube with a hollow bore.

Referring to FIGS. 1B-2, a repair device 10 is portrayed in contact with a defect comprising the inner surface 2, the outer surface 3 and a repair device void 4. The repair device 10 may comprise a first expandable barrier 20, or inlay, which may be radially symmetric and connected to a second barrier 30, or overlay, which may be expandable and also radially symmetric. In alternative embodiments, at least one barrier may be asymmetrical. The inlay 20 may be coupled to a connection member 40, (shown in FIG. 3) which defines a longitudinal axis of the device. In this and other embodiments, the connection member may be integrally formed with the inlay. In alternative embodiments, it may be formed separately from the inlay. The inlay 20 may be in communication with the overlay 30 through the connection member 40. The repair device may also comprise a first insertion tube 70, which may be an inlay inserter tube and a second insertion tube 80, which may be an overlay inserter tube. Positioned between the inlay 20 and the overlay 30 of the device 10 is a seal 60. The repair device void 4 is defined as the space between the inlay 20 and the overlay 30.

Referring to FIGS. 3-7, the inlay 20 comprises an inlay outer wall 26 and an inlay inner wall 28. In addition the inlay 20 features an inlay distal portion 24 and an inlay proximal portion 22 which may engage the inner surface 2 of the defect. The inlay 20 may comprise different configurations, a collapsed or compact configuration (not shown) and an expanded configuration. The inlay 20 may expand after passing through the defect opening to obliterate, or completely cover the defect opening from the inside of the defect interior space. Instead of expanding equally in all dimensions the inlay may expand more laterally or radially relative to the longitudinal axis, wherein the diameter increases in a "pancake-like" geometry to a diameter greater than the widest lateral dimension of the defect opening. The connection member 40 (shown in FIG. 3) extends proximally from the inlay 20 and may pass through the center of the seal 60 and the center of the overlay 30. The seal 60 resembles a flexible, ring-like tube with a void 62 extending longitudinally there through. The connection member 40 is configured to engage the overlay 30 and a proximal end of the connection member 40 may circumferentially and releasably engage the distal end of the first inserter tube 70. The first inserter tube 70 may comprise a first inserter tube bore 72 extending longitudinally through the center of the first inserter tube 70.

The connection member 40 may define a longitudinal axis along which the overlay 30 is configured to slide to alter the distance of separation between the inlay 20 and overlay 30. The connection member 40 may comprise a plurality of ring like notches or cut outs 44 along the periphery of the connection member which engage the overlay 30 in an overlay bore 35 which may pass through the geometric center of the overlay 30. The overlay bore 35 may narrow toward one end of the overlay bore 35, which creates a collar 36 that complementarily engages the notches 44 and allows the overlay 30 to advance toward the inlay 20. The notches 44 function as stops to prevent retraction of the overlay 30 away from the inlay 20 and lock the position of the overlay 30 relative to the connection member 40. The connection member 40 may use other means to prevent retraction back through the overlay bore 35 including barbs, ratchet teeth, high-friction contact surfaces, or other methods well known in the art. The connection member 40 may further comprise a connection member bore 42 passing longitudinally through the connection member 40 to allow access to the inlay 20 for introduction of gas, liquid or other means for expanding the inlay 20 including introducing a wire (not shown) through the connection member bore 42, in which the wire may radially expand and/or radially reinforce the inlay 20. Fluid used to expand the inlay 20 may include but is not limited to air, saline solution, hydrogel, silicone, curable adhesives and polyvinyl acetate (PVA). An expansion tool comprising a first catheter assembly may be connected to the connection member to introduce fluid through a first catheter lumen into the connection bore 42.

In alternative embodiments, the first inserter tube 70 may comprise the wire and perform as an expansion tool wherein the wire may advance through the first inserter tube bore 70 to expand the inlay. Other means of expansion may be a pull wire (not shown) which engages the inlay and passes through the connection member bore 42 and, when pulled, radially expands the inlay 20. The connection member bore 42 may be accessible through the first inserter tube bore 72.

The inlay 20 may further comprise a reinforcing body 50, and may resemble a Molly anchor, which comprises a plurality of ribs residing within the inlay 20, or deployable within the inlay 20, and engaging the inner inlay wall 28. The reinforcing body 50 connects to the distal end of the connection member 40 as well as the distal end of the inlay 20 and functions similar to a flexible wire basket or cage in order to radially expand and/or reinforce the inlay 20 as the connection member 40 is drawn proximally through the overlay 30 causing an increase in the radius of the inlay 20 and causing it to engage the inner surface of the defect 2. The reinforcing body 50 may comprise an alternate support means other than a flexible basket or cage with ribs, for example a flexible wire ring, a mesh construct, or another reinforcing construct well known in the art may be used. The inclusion of the reinforcing body in the inlay may prevent unintended retraction of the first barrier.

The seal 60 may comprise a bore passing longitudinally through the seal which would allow for passage of the connection member 40. Toward the distal end of the seal 60 the diameter of the seal 60 increases with a "flare-like" geometry. A seal rim 64 of the seal 60 may circumferentially engage the inlay outer wall 26 at the inlay proximal portion 22. The seal 60 may be at least partially collapsible to allow variations in positioning between the inlay 20 and overlay 30 while still adequately functioning to seal the junction between the inlay and overlay.

The overlay 30 may comprise a dome-like cup 33 with a rim 31 equidistant from the dome-like cup 33 geometric center. An inner overlay wall 32 of the overlay 30 faces the defect and an outer overlay wall 34 faces away from the defect. The rim 31 of the overlay 30 circumferentially engages the outer surface 3 of the defect obliterating, or completely covering, the defect opening. A hollow first cylinder 38 may protrude distally from the center of the inside of the dome-like cup 33 of the overlay 30 with a bore larger than the overlay bore 35. The first cylinder 38 is configured to circumferentially engage with the seal 60 on the outer wall of the cylinder 38. The overlay may also comprise a hollow second cylinder 39 proximally protruding from the center of the dome-like cup 33 of the outer overlay wall 34. The second cylinder 39 may comprise a bore substantially the same size as the bore of the first cylinder 38. The most proximal portion of the overlay 30 (or the distal end of the second cylinder 39 as extending from the outer overlay wall 34, one and the same) may circumferentially and releasably engage a second inserter tube 80 at a distal end of the second inserter tube 80. The second inserter tube 80 may comprise a second bore 82 extending longitudinally there through. The first inserter tube 70 may be positioned at least partially within the second bore 82 of the second inserter tube 80.

Figure 4:
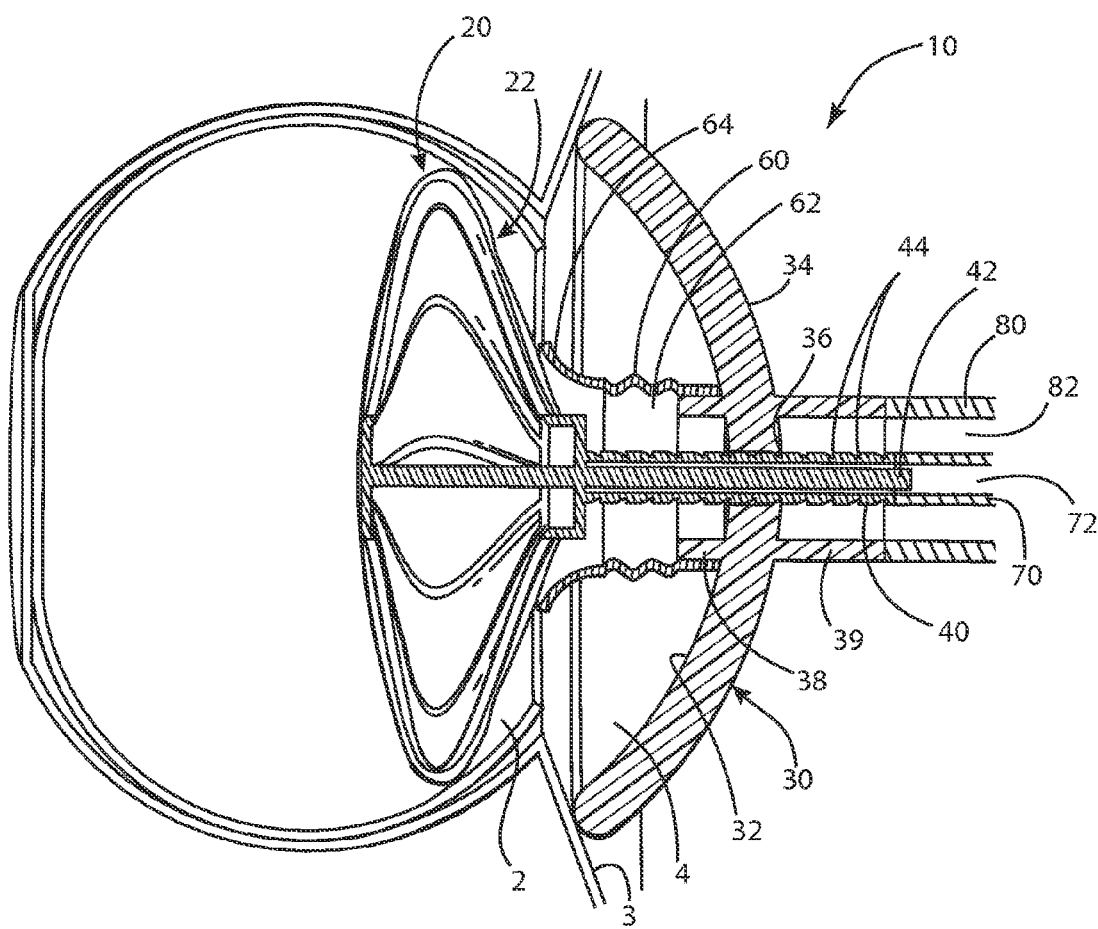
FIG. 4 illustrates an enlarged cross sectional side view of a portion of the defect repair device of FIG. 1 with the seal, the inlay, the connecting member, and the overlay.
Figure 5:
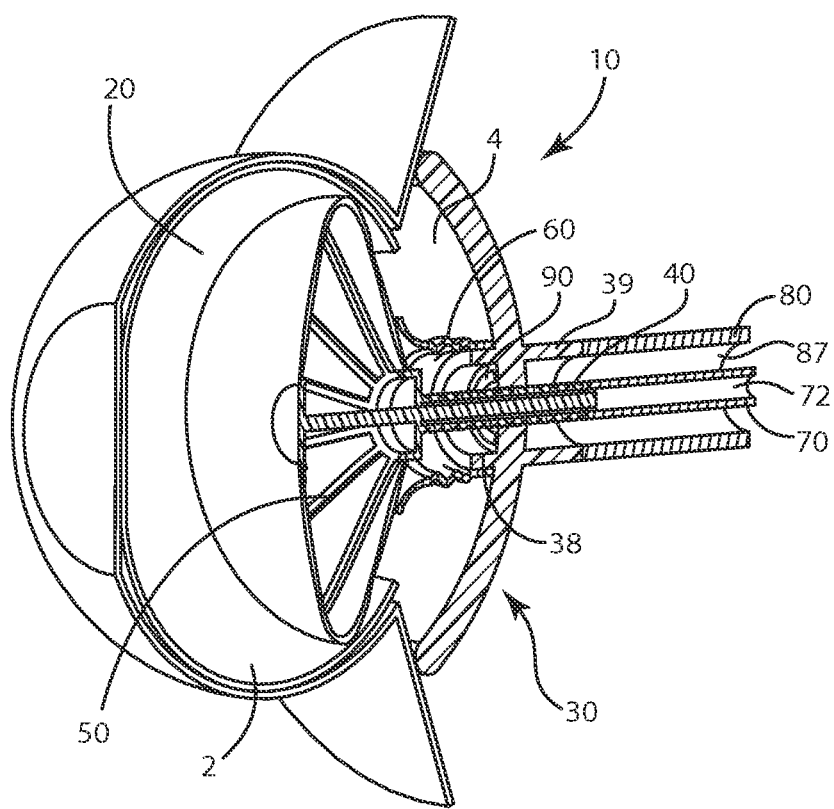
FIG. 5 illustrates a distal cross sectional perspective view of the defect repair device of FIG. 1 with the defect, the inlay, the connection member having a plurality of glue ports, and the overlay.
Figure 6:
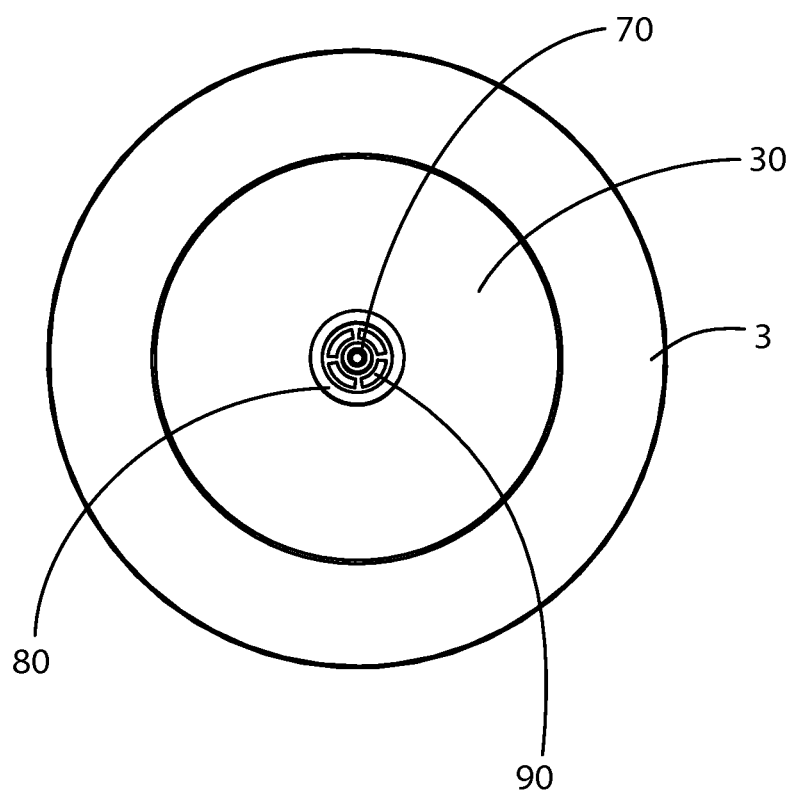
FIG. 6 illustrates a proximal axial view of the defect repair device of FIG. 1 with the overlay, the inlay inserter tube, the overlay inserter tube and the connection member with a plurality of glue ports.
Figure 7:
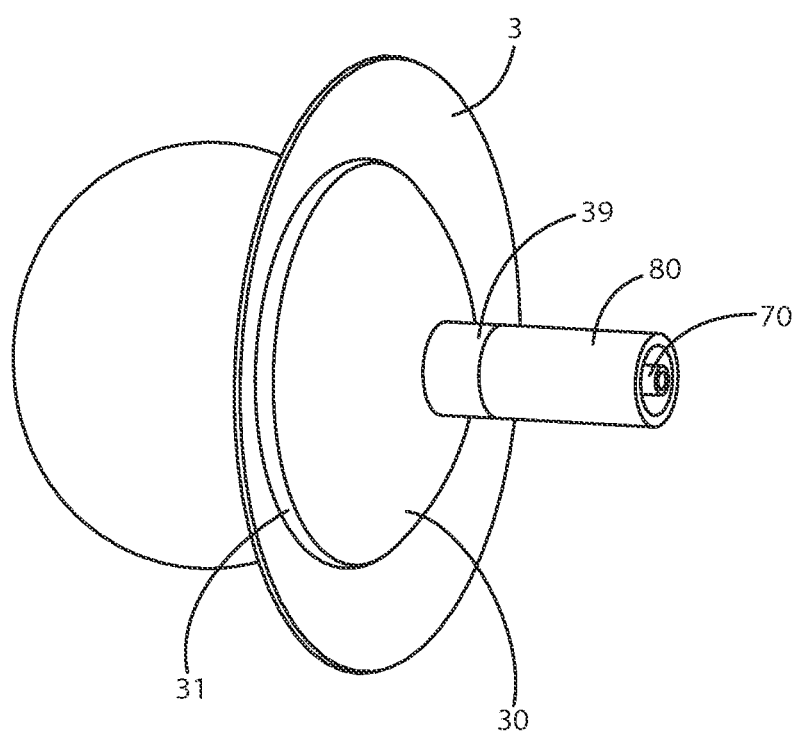
FIG. 7 illustrates a proximal perspective view of the defect repair device of FIG. 1 with the overlay, the inlay inserter tube and the overlay inserter tube.

Referring to FIGS. 4 and 5, the overlay 30 may also comprise at least one glue port 90 which passes through the body of the overlay 30 within the first and second cylinders 38, 39. The glue port 90 may be in communication with the seal void 62 and the second bore 82. Fibrin glue, or other sealing material, may be introduced through the overlay inserter tube 80 to pass through the second bore 82 and be expelled through a glue port 90, into the seal void 62, and into the repair device void 4 between the inlay 20 and overlay 30, which further secures and/or seals the inlay 20 and overlay 30 to the defect. The seal rim 64 allows for one way passage of fibrin glue outside of the seal void 62 into the repair device void 4 and prevents CSF from leaking through the seal 60 back through a glue port 90 because the pressure from the fibrin glue pushes the seal rim 64 against the inlay proximal portion 22. A second catheter assembly may be connected to the second bore 82 to introduce the sealing material through a second catheter lumen into the second bore 82 and glue ports 90.

For this and other embodiments, the repair device may be made from either bio-absorbable or non-absorbable or a combination of both types of materials including but not limited to nylon, polypropylene, polyester, polyurethane, polyvinyl chloride, polyethylene terephthalate (PET), Teflon, Dacron, polytetrafluoroethylene (PTFE), expanded polytetrafluoroethylene (ePTFE), polyethylene, silicone, polyaryletherthereketone (PEEK), hydrogel, poly 1-lactic acid (PLA), polyglycolic acid (PGA), tricalcium phosphate (TCP), Nitinol, stainless steel, titanium, and other biocompatible materials.

One method of using the repair device 10 is to introduce the inlay 20 in a collapsed state wherein the inlay 20 is at its smallest diameter. The inlay 20 may be introduced into the defect interior space with the first inserter tube 70. Once in the desired location, the inlay 20 of the repair device 10 may be expanded in diameter to obliterate the defect opening. There may be only slight expansion in the inlay 20 height but more significant radial expansion The materials of construction are soft, compliant, and malleable, in order to prevent injury to the adjacent soft-tissue and vascular structures. Once a watertight reconstitution was confirmed, the inlay 20 may be contracted slightly, reducing its height but maintaining its diameter.

The seal 60 and overlay 30 may then be placed in each of their respective appropriate locations using the second inserter tube 80 with the connection member 40 passing through the seal 60 and overlay 30. The overlay may be secured in place using suturing, nailing, riveting, adhering, or stapling techniques as well as other anchoring means, including the connection member notches 44 interacting with the overlay collar 36 to lock the position of the overlay relative to the connection member. The overlay 30 may be "ratcheted" up the connection member 40 through the use of the notches 44 and the collar 36, which brings the inlay 20 and overlay 30 in closer proximity and which may at least partially collapse the seal 60. Fibrin glue may then be introduced through the second inserter tube bore 82 further passing through the at least one glue port 90 and entering the seal void 62. The fibrin glue may be introduced into the repair device 10 until the glue enters the repair device void 4 by passing over the flare-like geometry of the seal 60 creating a pressure valve of the seal rim 64. Because of the flare-like geometry of the seal and the engagement of the seal rim 64 against the inlay 20 the pressure valve of the seal rim 64 prevents CSF from leaking back through the seal void 62 and through the at least one glue port 90. The inlay 20 in contact with the surface of the inner surface 2 acts as a shield to prevent the fibrin glue from migrating past this area of contact into the intradural space distal to the inlay 20. Similarly, the contact between the overlay 30 and the surface of the outer surface 3 retains the fibrin glue in the repair device void 4.

The connection member 40 may further slide up the collar 36 compressing the inlay 20 and overlay 30 more tightly against the defect surfaces for additional fixation and/or sealing. The first and second inserter tubes 70, 80 may then be removed from the inlay 20 and overlay 30. In the final implant construct, the connection member 40 may protrude from the outer overlay wall 34.

Alternatively the overlay 30 may be similar to the inlay 20 in its structure with a reinforcing body 50 and similar means of expansion. However, the communication between the inlay 20 and overlay 30 may be as previously described above using the connection member 40 and the seal 60.

Figure 8:
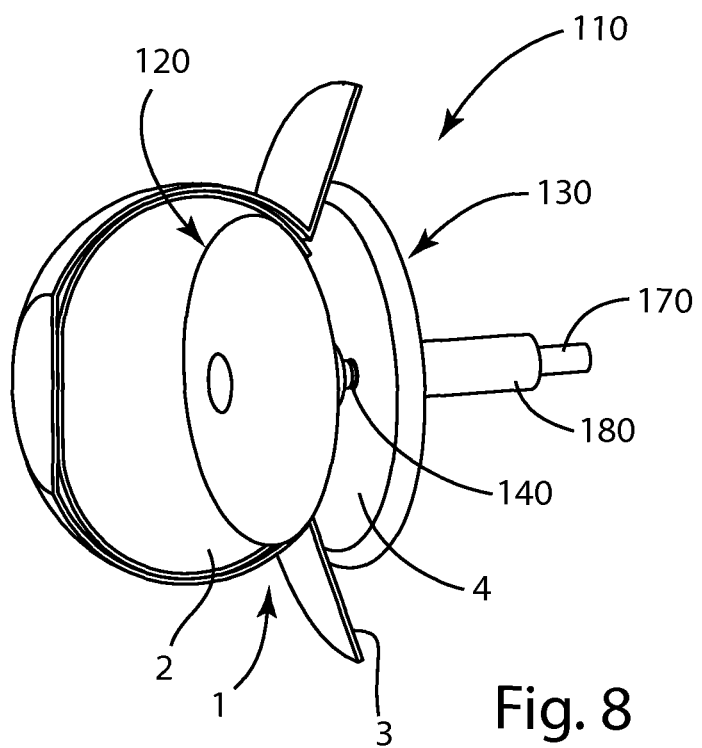
FIG. 8 illustrates a distal perspective view of the defect in cross section with an alternate embodiment of the defect repair device of FIG. 1 with an inlay, an overlay, an inlay inserter tube and an overlay inserter tube.
Figure 9:
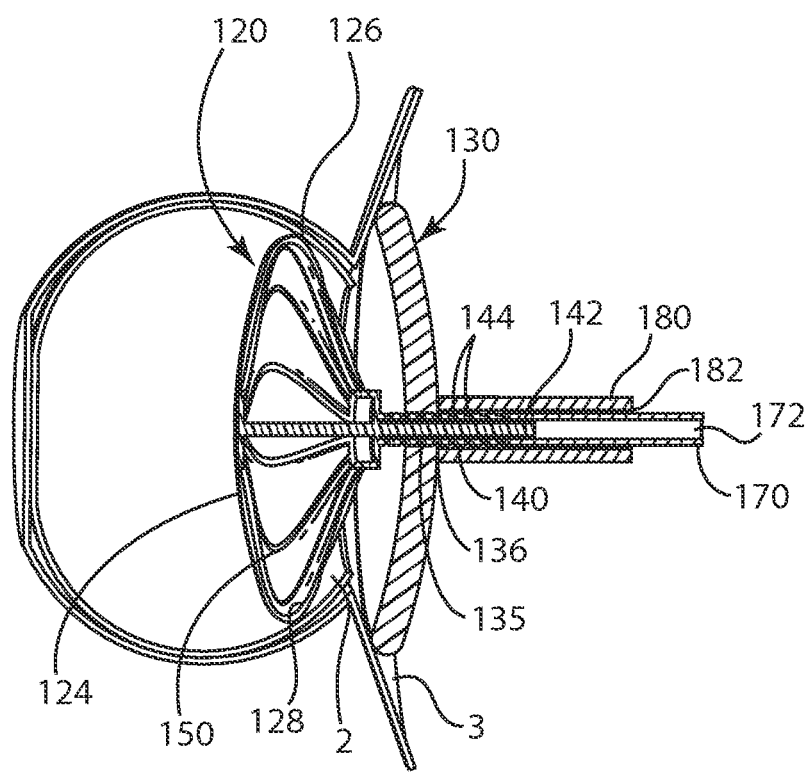
FIG. 9 illustrates a cross sectional side view of the defect and the defect repair device of FIG. 8 with the inlay the overlay, the inlay inserter tube, and the overlay inserter tube, a connecting member, and a reinforcing body in the inlay.
Figure 10:
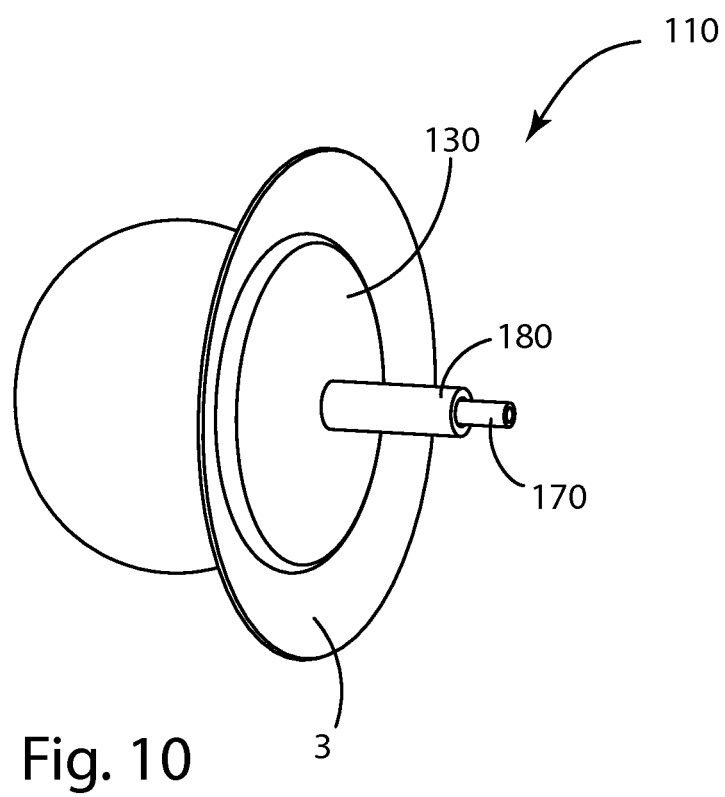
FIG. 10 illustrates a perspective proximal view of the defect repair device of FIG. 8 with the inlay inserter tube, the overlay inserter tube and the overlay.

FIGS. 8-10 illustrate an alternate embodiment of repair device with an inlay, an overlay and a connection member. Referring to FIG. 8, an alternate embodiment of a repair device 110 includes the same elements of the previously described embodiment with a first expandable barrier or inlay 120 and a second barrier or overlay 130 which may be expandable. A connection member 140 may be coupled to the inlay and may be configured to engage the overlay 130 and a proximal end of the connection member 140 and may circumferentially and releasably engage a first inserter tube 170 which may comprise a first inserter tube bore 172. A second inserter tube 180 may comprise a second inserter tube bore 182 passing longitudinally through the second inserter tube 180 and may fit at least partially around the first inserter tube 170.

Referring to FIGS. 9-10, the interaction of the inlay 120 and the overlay 130 is similar to that of repair device 10 in that the connection member 140 may define a longitudinal axis and comprise notches 144 that interact with a collar 136 positioned within a bore 135 of the overlay 130. This collar 136 may engage the notches 144 such that the connection member 140 may move proximally but the notches 144 interact with the collar 136 to prevent withdrawal of the connection member back through the overlay bore 135. The distal end of the inserter tube 170 circumferentially engages the proximal end of the connection member 140. Similar to the previous embodiment, a connection member bore 142 may pass longitudinally through the connection member 140. The connection member bore may be in communication with the first inserter tube bore 172 allowing for passage of gas, liquid, a wire, or other means to expand the inlay 120. This alternate embodiment of the repair device 110 lacks the seal 60 present in the previous embodiment, however it is appreciated that this may be easily incorporated therein as desired. The means for fixating the repair device 110 include the same means previously described such as suturing, nailing, riveting, adhering, or stapling techniques as well as use of fibrin glue.

Similar to the previous embodiment, the first inserter tube 170 may act as an expansion tool and cause inlay 120 to be expanded by advancing a wire (not shown) through the first inserter tube 170. The wire may also provide reinforcement to the inlay 120 to prevent subsequent collapse and detachment from the defect. Fluid may be also be used to expand the inlay 120; suitable fluids include, but are not limited to, air, saline solution, hydrogel, silicone, curable adhesives, and polyvinyl acetate (PVA).

Similar to the previous embodiment the inlay 120 may resemble a Molly anchor and comprise a reinforcing body 150 comprised of a plurality of ribs deployable within the inlay 120, or residing within the inlay 120, and engaging an inner inlay wall 128. The reinforcing body 150 connects to the distal end of the connection member 140 as well as the distal end of the inlay 124 and functions similar to a flexible wire basket or cage in order to radially expand and/or reinforce the inlay 120 as the connection member 140 is drawn proximally through the overlay 130 causing an increase in the radius of the inlay 120 and causing an outer wall of the inlay 126 to engage the inner surface of the defect 2. The reinforcing body 150 may comprise an alternate support means other than a flexible basket or cage with ribs, for example a flexible wire ring (not shown), a mesh construct, or another reinforcing construct known in the art may be used to both expand and reinforce the inlay 120.

This repair device 110 may be comprised of many different materials, including those recited herein for the previous embodiment.

One method of using the repair device 110 would be similar to that described in the previous embodiment with the exception of the seal and the introduction of the fibrin glue. The first inserter tube 170 may introduce the inlay 120 into the defect in a collapsed state, with the inlay 120 at its smallest diameter. Once in the desired location, the inlay 120 of the repair device 110 may be expanded to a diameter greater than the lateral dimension of the defect opening, obliterating, or completely covering the defect opening. There may be only slight expansion in the inlay 120 height but more significant radial expansion. The materials of construction are soft, compliant, and malleable, in order to prevent injury to the adjacent soft-tissue and vascular structures. Once a watertight reconstitution was confirmed, the inlay 120 may be contracted slightly, reducing its height but maintaining its diameter.

The overlay 130 may then be placed in its appropriate location using the second inserter tube 180 with the connection member 140 passing through the overlay 130. The overlay may be secured in place using suturing, nailing, riveting, adhering, or stapling techniques as well as other anchoring means, including the connection member notches 144 interacting with the overlay collar 136. The overlay 130 may be "ratcheted" up the connection member 140 through the use of the notches 144 and the collar 136 bringing the inlay 120 and overlay 130 in closer proximity.

The collar 136 of the overlay 130 may further slide up the connection member 140 compressing the inlay 120 and overlay 130 more tightly against the defect surfaces for additional fixation and/or sealing. The first and second inserter tubes 170, 180 may then be removed from the inlay 120 and overlay 130. In the final implant construct, the connection member 140 may protrude from the outer overlay wall 134. In this embodiment fibrin glue may be introduced locally, topically, into, or around the repair device 110 by any means known in the art.

Figure 11:
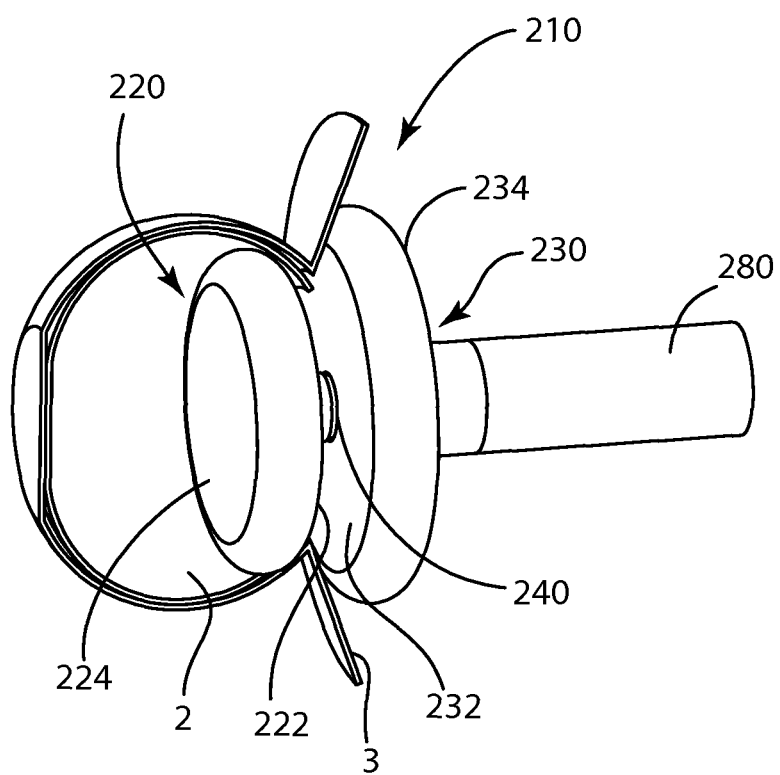
FIG. 11 illustrates a distal perspective view with the defect in cross section of an alternate embodiment of the defect repair device of FIG. 1 with an inlay balloon, an overlay balloon, a connecting member and an overlay inserter tube.

FIGS. 11-14 illustrate an alternate embodiment of a repair device using a balloon like mechanism with an inlay, an overlay and a connection member. Referring to FIG. 11, an alternate embodiment of a repair device 210 includes the same elements of the previously described embodiment with a first expandable barrier or inlay 220 positioned on one side of the defect opening and a second expandable barrier or overlay 230 on an opposing side of the defect opening. A connection member 240 may be coupled to the inlay 220 and may be configured to engage the overlay 230. A second inserter tube 280 may circumferentially and releasably engage the overlay 230 at the proximal end of the overlay 230 and at the distal end of the second inserter tube 280.

Figure 12:
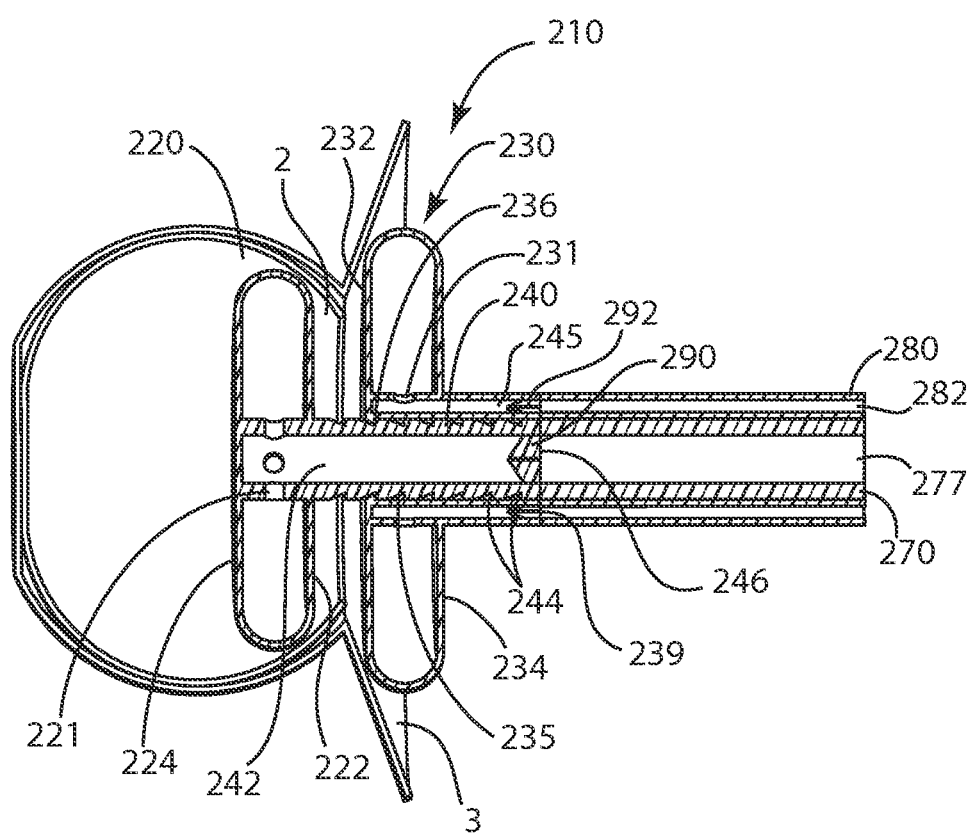
FIG. 12 illustrates a cross sectional side view of the defect and the defect repair device of FIG. 11 with the inlay balloon with connection portion, the overlay balloon, an inlay inserter tube, the overlay inserter tube, an inlay tube seal, and an overlay tube seal.
Figure 13:
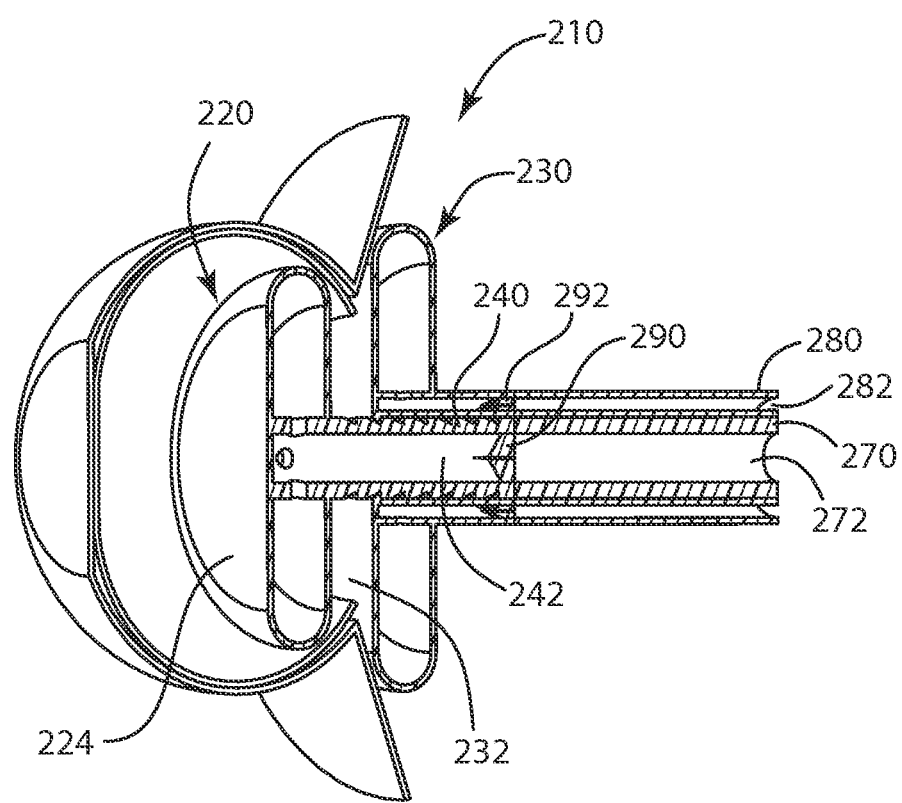
FIG. 13 illustrates a cross sectional perspective distal view of the defect and the defect repair device of FIG. 11 with the inlay balloon, the overlay balloon, the inlay inserter tube, the overlay inserter tube, the connecting member, the inlay tube seal, and the overlay tube seal.
Figure 14:
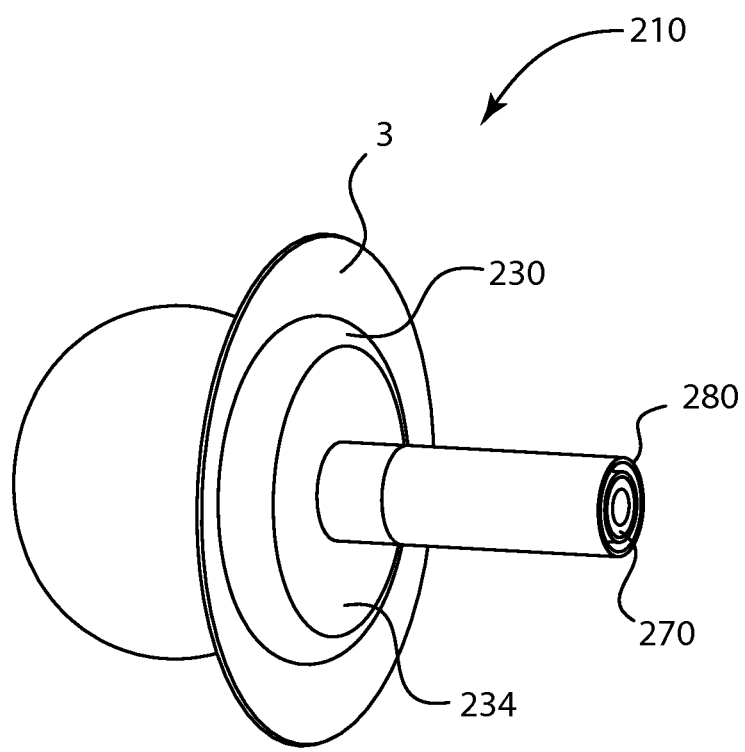
FIG. 14 illustrates a perspective proximal view of the defect repair device of FIG. 11 with the overlay balloon, the inlay inserter tube, and the overlay inserter tube.

Referring to FIGS. 12-14, the inlay 220 comprises a balloon which expands into a "pancake-like" geometry to obliterate the defect on one side of the defect opening and to engage the inner surface 2 of the defect. The inlay 220 expands laterally without much expansion in the inlay 220 height. This lateral expansion may be accomplished by having a more rigid material on a distal portion of the inlay 224 and the proximal portion of the inlay 222 and a more compliant material along the circumferential lateral ends of the inlay 220. Similarly, the overlay 230, which comprises a second balloon, may expand laterally to obliterate the defect opening and engage the outer surface 3 of the defect. The overlay 230 may include the same rigid material on the distal portion of the overlay 232 and the proximal portion of the overlay 234 and a more compliant material along circumferential lateral ends of the overlay 230. In their expanded configurations, both the inlay 220 and the overlay 230 may each have a diameter greater than the lateral dimension of the defect opening. Each balloon disclosed herein may comprise an elastomeric sheath comprised of silicone, polyurethane, or hydrogel, among other materials. The elastomeric sheath may comprise zones with varying levels of compliance or elasticity, such that the balloon inflates to a greater extent in some zones than in others.

The connection member 240 may define a longitudinal axis along which the overlay 230 is configured to slide to alter the distance of separation between the inlay 220 and overlay 230. The connection member 240 may comprise a plurality of ring like stops, notches or cut outs 244 along the periphery of the connection member which engage the overlay 230 in a first overlay bore 235 which may pass through the geometric center of the overlay 230. The first overlay bore 235 may comprise a collar 236 that complementarily engages the notches and allows the overlay 230 to advance toward the inlay 220 but prevents retraction of the overlay 230 away from the inlay 220. Adjacent to, but separate from, the first overlay bore is a second overlay bore 245 which may extend longitudinally through the overlay 230 and is used for balloon inflation. The connection member 240 may use other means to prevent retraction back through the first overlay bore 235 including barbs, ratchet teeth, high-friction contact surfaces, or other methods well known in the art. The connection member 240 may further comprise a connection member bore 242 passing longitudinally through the connection member 240 to allow access to the inlay 220 for introduction of gas, liquid or other means for expanding the inlay 20 including introducing a wire (not shown) through the connection member bore 242, in which the wire may radially expand and/or reinforce the inlay 220. Fluid used to expand the inlay may include but is not limited to air, saline solution, hydrogel, silicone, curable adhesives and polyvinyl acetate (PVA).

A proximal portion 246 of the connection member 240 may comprise an inlay tube seal 290 which allows introduction of fluid or gas for expanding the inlay 220, but prevents egress of the same fluid or gas. This inlay tube seal 290 may be or function similar to a pressure valve or other one-way valve. Similarly a proximal portion of the overlay 239 may comprise at least one overlay tube seal 292 which may allow introduction of gas or fluid into the second overlay bore 245 for expanding the overlay 230 but prevents egress of the same fluid or gas. The overlay tube seal 292 may be or function similar to a pressure valve, or other one-way valve.

A first inserter tube 270 may be circumferentially and releasably coupled to the proximal portion 246 of the connection member 240. The first inserter tube comprises a first inserter longitudinal bore 272 passing there through that provides access to the connection member bore 242 through the inlay tube seal 290. The first inserter tube 270 may reside at least partially within the second inserter tube 280 which may comprise a second inserter longitudinal bore 282. The second inserter longitudinal bore 282 is large enough such that when the first inserter tube 270 is positioned within the second inserter tube bore 282 the at least one overlay tube seal 292 still maintains fluid access for expansion of the overlay 230.

The inlay 220 and overlay 230 may also comprise fluid ports 221, 231. The inlay fluid ports 221 allow for fluid to be introduced from the connection member bore 242 into the inlay 220. Likewise, the overlay fluid ports 231 allow fluid to be introduced from the second overlay bore 245 into the overlay 230. A wire may alternately be used to expand and/or reinforce the inlay 220 and the overlay 230.

One method of using the repair device 210 is be similar to that described in the previous embodiments with the exception that the inlay and overlay 230 are both expanded by inflation via a gas or fluid. The first inserter tube 270 may introduce the inlay 220 into the defect opening in a collapsed state, with the inlay 220 at its smallest diameter. Once in the desired location inside the defect interior space, the inlay 220 of the repair device 210 may be expanded through introduction of gas or fluid into the inlay 220 to obliterate the defect opening. There may be only slight expansion in the inlay 220 height because of the rigidity of the material on the proximal and distal ends 222, 224 of the inlay 220. The materials of construction are soft, compliant, and malleable, in order to prevent any injury to the adjacent soft-tissue and vascular structures. Once a watertight reconstitution is confirmed, the inlay 220 may be contracted slightly, reducing its height but maintaining its diameter.

The overlay 230 may then be placed in its appropriate location using the second inserter tube 280 with the connection member 240 passing through the overlay 230. Once in the desired location on the opposing side of the defect opening from inlay 220, the overlay 230 may be expanded through the introduction of gas or fluid to obliterate the defect as well. There may be only slight expansion in the overlay 230 height because of the rigidity of the material on the proximal and distal ends 232, 234 of the inlay 230. The repair device 210 may be secured in place using suturing, nailing, riveting, adhering, or stapling techniques as well as other anchoring means, including the connection member notches 244 interacting with the overlay collar 236. The overlay 230 may be "ratcheted" up the connection member 240 through the use of the notches 244 and the collar 236 bringing the inlay 220 and overlay 230 in closer proximity.

The overlay 230 may further slide up the connection member 240 through interaction of the collar 236 and the notches 244 compressing the inlay 220 and overlay 230 more tightly against the defect surfaces for additional fixation and/or sealing. The first and second inserter tubes 270, 280 may then be removed from the inlay 220 and overlay 230. In the final implant construct, the connection member 240 may protrude from the outer overlay wall 234. In this embodiment fibrin glue may be introduced locally, topically, into, or around the repair device 210 by any means known in the art. Alternately, connection member 240 may comprise a separate bore, and ports, for introduction of fibrin glue into the repair device void.

Figure 15:
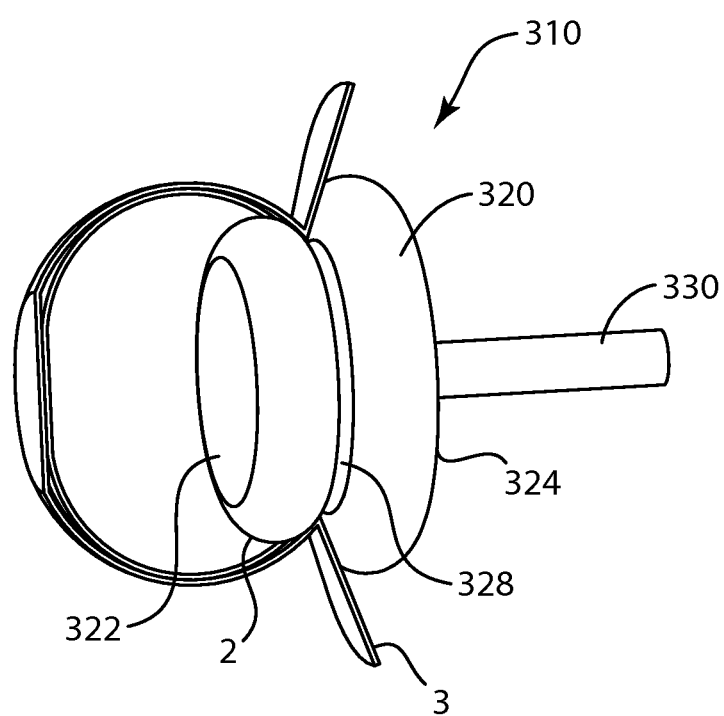
FIG. 15 illustrates a distal perspective view with the defect in cross section of an alternate embodiment of the defect repair device of FIG. 1 with a single balloon barrier having a first inlay portion and a second overlay portion and a balloon delivery tube.
Figure 16:
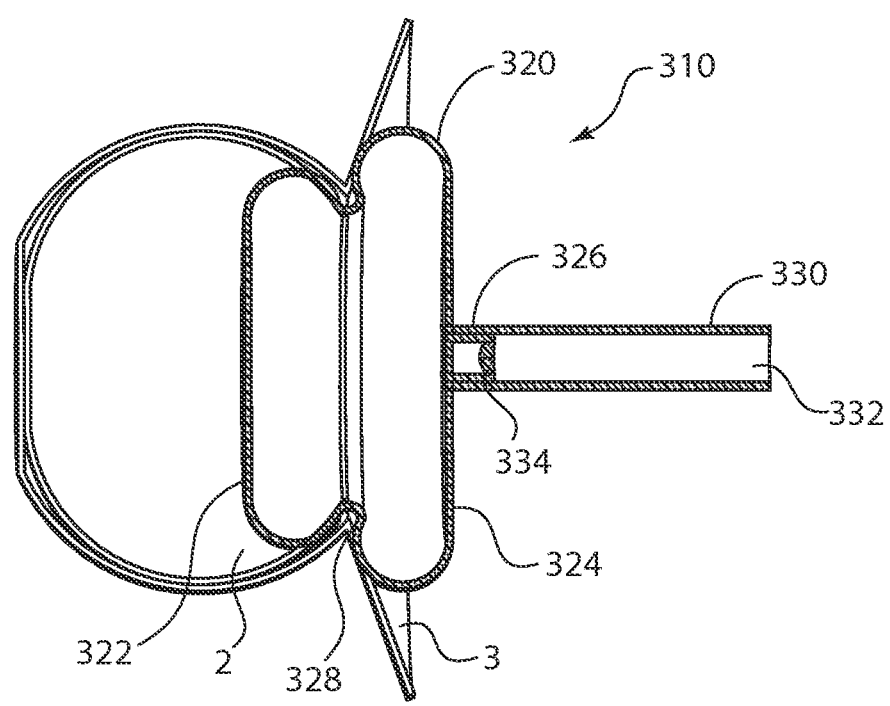
FIG. 16 illustrates a cross sectional side view of the defect repair device and defect of FIG. 15 with the single balloon barrier, the balloon delivery tube and a restricting neck on the balloon barrier.
Figure 17:
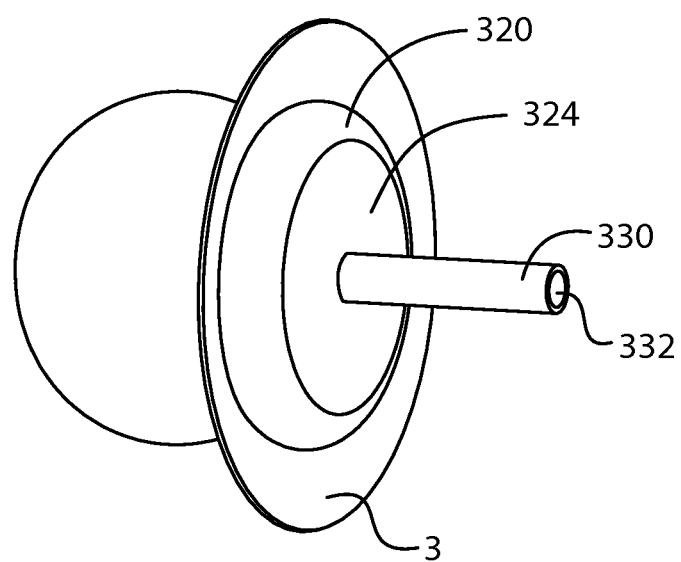
FIG. 17 illustrates a perspective proximal view of the device of FIG. 15 with a proximal portion of the single balloon barrier and the balloon delivery tube.

FIGS. 15-17 illustrate an alternate embodiment of a repair device using a single balloon like mechanism having a constriction between a distal and proximal portion. Referring to FIG. 16, repair device 310 may comprise an expandable barrier 320 with a distal portion 322, a proximal portion 324 and a ring 328 forming a neck between the distal and proximal portions 322, 324. Each portion of the expandable barrier 320 may expand laterally without much expansion in the expandable barrier 320 height. This lateral expansion may be accomplished by having a more rigid material on a distal end of the distal portion 322 and the proximal end of the proximal portion 324 and a more compliant material along the circumferential lateral sides of the expandable barrier 320. The expandable barrier 320 may also comprise a pre-shaped balloon which inflates to a predetermined shape. The ring 328 may traverse the defect opening and may be comprised of the same or similar material as the proximal and distal portions 322, 324. The ring 328 may comprise less compliant material then the circumferential lateral sides of the expandable barrier, and in some embodiments the ring 328 may be rigid. The expandable barrier 320 may comprise a hollow cylinder 326, with a longitudinal axis extending proximally from the proximal end 324 of the expandable barrier 320. The hollow cylinder 326 may also comprise a seal or valve 334 used for balloon inflation. The repair device 310 may also comprise an inserter tube 330 which may comprise a bore 332 extending longitudinally there through. The inserter tube 330 may circumferentially and releasably engage the cylinder 326.

One method of using the repair device 310 may be to introduce the expandable barrier 320 into the defect in a collapsed state, with the expandable barrier 320 at its smallest diameter. The expandable barrier 320 may be inserted into the defect using the inserter tube 330, until distal portion 322 is inside the defect interior space, and proximal portion is outside of the defect opening. Once in the desired location traversing the defect, the expandable barrier 320 of the repair device 310 may be expanded through the introduction of gas or fluid into the expandable barrier through the inserter tube bore 332, the hollow cylinder 326 and into the expandable barrier 320, in order to obliterate the defect opening. The expandable barrier 320 may expand laterally until the distal portion 322 positioned distal the rigid ring 328 engages the inner surface 2 of the defect and the proximal portion 324 positioned proximal the rigid ring 328 engages the outer surface 3 of the defect. There may be only slight expansion in the expandable barrier 320 height because of the rigidity of the material on the proximal and distal ends of the expandable barrier 320. The ring 328 may also expand with introduction of fluid or gas but not to the extent of the proximal and distal portions 322, 324. The materials of construction are soft, compliant, and malleable, in order to prevent any injury to the adjacent soft-tissue and vascular structures. Once a watertight reconstitution is confirmed, the expandable barrier 320 may be contracted slightly, reducing its height but maintaining its diameter. The inserter tube 330 may be removed after the proper placement and expansion of the expandable barrier 320. In this embodiment fibrin glue may be introduced locally, topically, into, or around the repair device 310 by any means known in the art.

Figure 18:
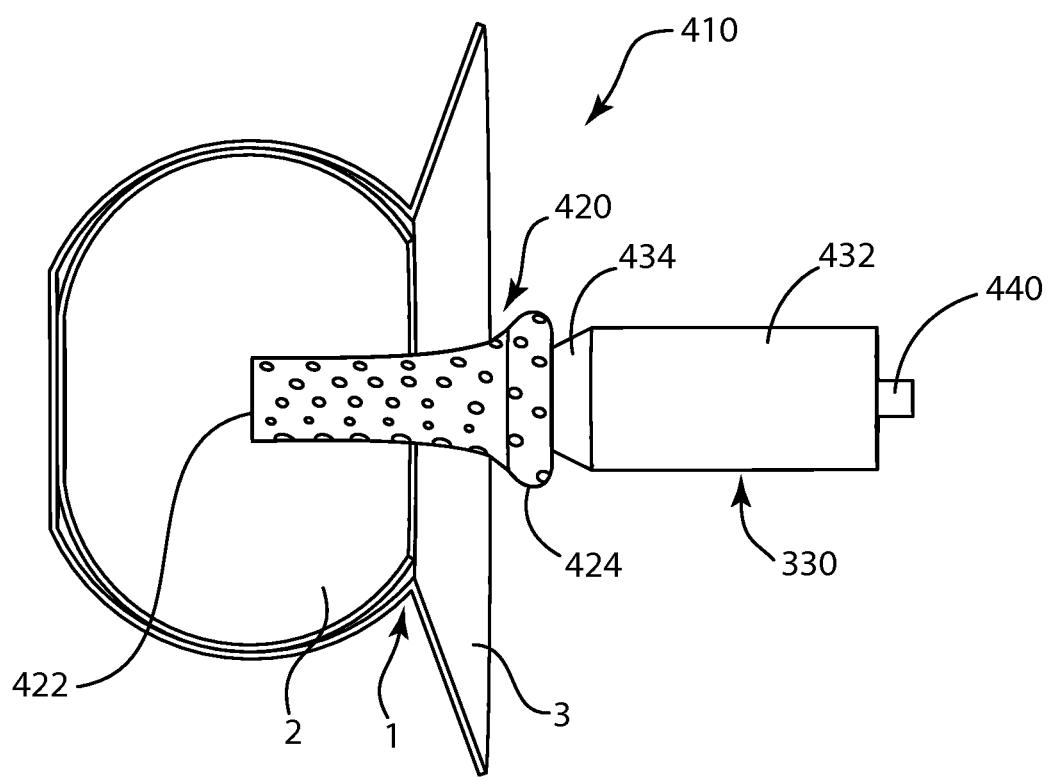
FIG. 18 illustrates a side view, with the defect in cross section, of an alternate embodiment of the device of FIG. 1 with an umbrella inlay, an umbrella insertion tube, and an umbrella insertion shaft.
Figure 19:
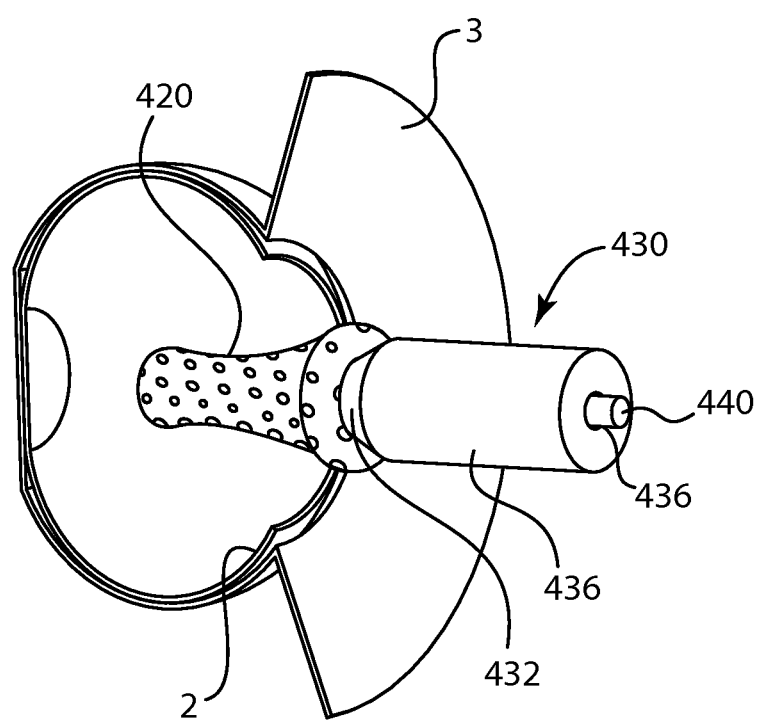
FIG. 19 illustrates a perspective proximal view of the device of FIG. 18 with the defect in cross section with the umbrella inlay, the umbrella insertion tube, and the umbrella insertion shaft.

FIGS. 18-24 illustrate an alternate embodiment of a repair device using an umbrella-like expandable barrier positioned inside a defect to interact with an inner surface of the defect and a second barrier which may be expandable. Referring to FIGS. 18 and 19, a repair device 410 may comprise an expandable barrier 420 in a collapsed state with distal end 422, which is fixed, and an expandable proximal portion 424. In its collapsed state the expandable barrier 420 is at its smallest diameter and able to be advanced through the defect opening. The repair device 410 may also comprise a plunger 430 and a connection member 440. The connection member 440 and plunger 430 may be used to position the expandable barrier within the defect interior space; however, inserter tubes (not shown) may also be used to position the repair device 410 within the defect. The plunger 430 may comprise a cylinder 432 and a cone like distal portion 434 which may circumferentially and releasably engage the expandable barrier 420 at the expandable proximal portion 424. The plunger 430 may also comprise longitudinal axis and a plunger bore 436 running longitudinally through the plunger 430. The connection member 440 may be coupled to the expandable barrier 420 and extends proximally from the expandable barrier 420. The connection member 440 may pass through the plunger bore 436.

Figure 20:
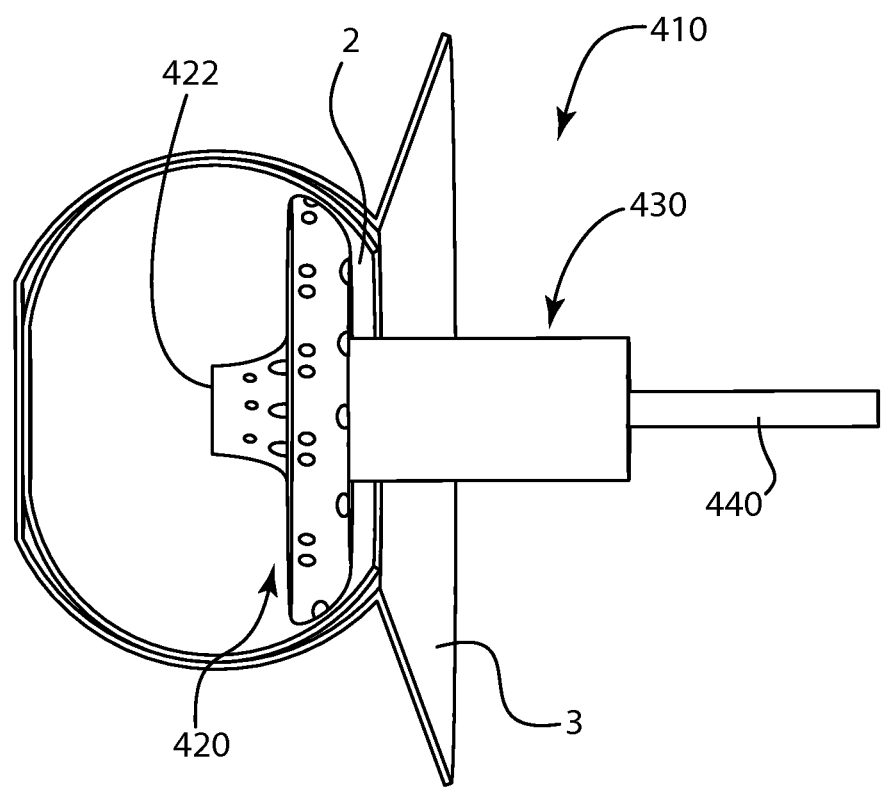
FIG. 20 illustrates a side view of the device of FIG. 18 with the defect in cross section with the umbrella inlay expanded within the defect, with the umbrella insertion shaft pushed distally toward a distal end of the umbrella inlay, and the umbrella insertion shaft.
Figure 21:
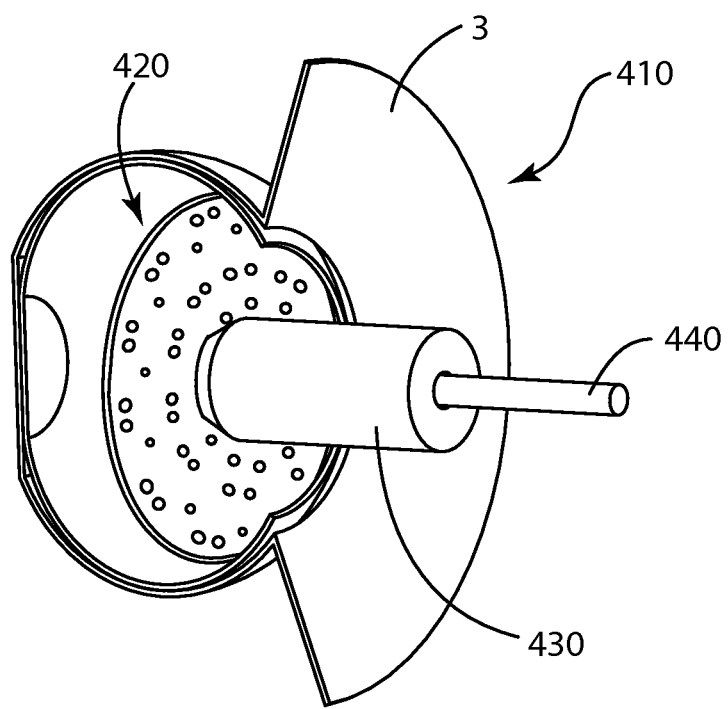
FIG. 21 illustrates a perspective proximal view of the device of FIG. 18 with the defect in cross section with the umbrella inlay expanded within the defect, with the umbrella insertion shaft pushed distally toward the distal end of the umbrella inlay, and the umbrella insertion shaft.

Referring to FIGS. 20 and 21, after the expandable barrier 420 is properly positioned within the defect interior space the plunger 430 is advanced toward the distal end of the expandable barrier 422. The expandable barrier 420 opens up or expands radially like an umbrella, to engage the inner surface 2 of the defect and obliterate the defect opening. The plunger 430 may then be removed from the repair device.

Figure 22:
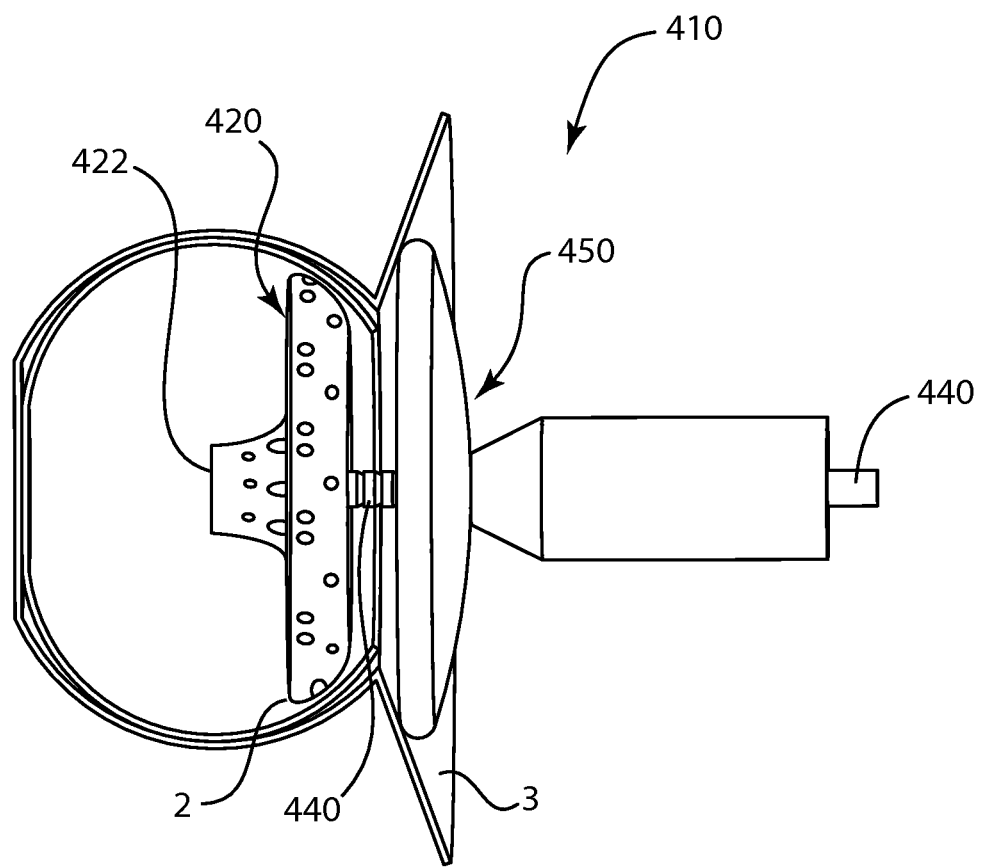
FIG. 22 illustrates a side view of the device of FIG. 18 with the defect in cross section with the expanded umbrella inlay within the defect, a connection member, an overlay, the umbrella inserter tube, and the umbrella inserter shaft.
Figure 23:
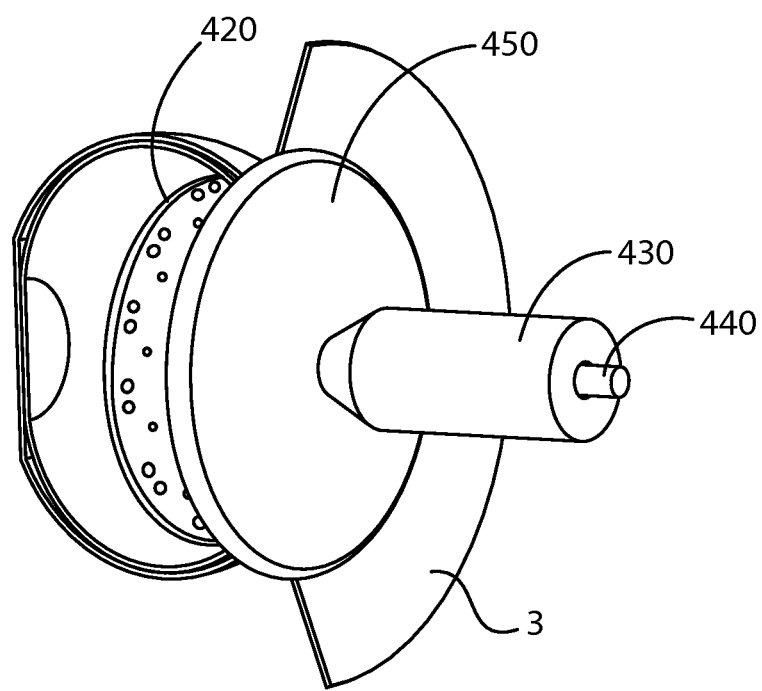
FIG. 23 illustrates a perspective proximal view of the device of FIG. 18 with the defect in cross section with the umbrella inlay expanded within the defect, the overlay, the umbrella inserter tube, and the umbrella inserter shaft.
Figure 24:
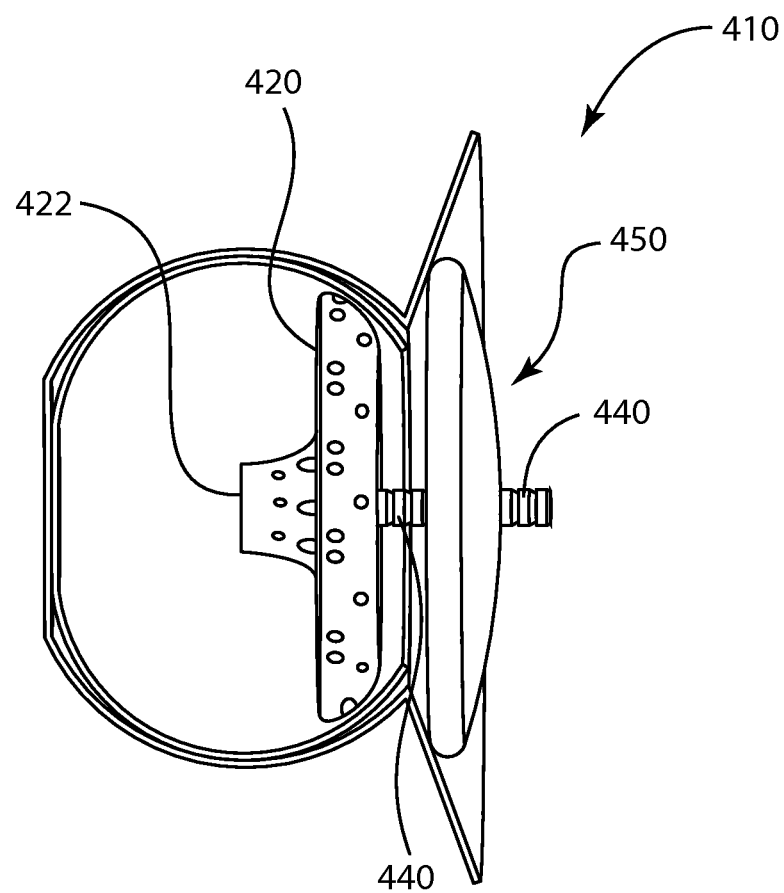
FIG. 24 illustrates a side view of the device of FIG. 18 with the defect in cross section the expanded umbrella inlay within the defect, the connection member, and the overlay.

Referring to FIGS. 22-24, a second barrier 450, which may also be expandable, may comprise a dome like cup similar to that of the previously embodied inlay 130 depicted in FIGS. 8-11. The second barrier 450 may comprise the same elements as those previously stated for the inlay 130 and may carry out the same function as depicted and described for FIGS. 8-11. One difference from the previous embodiment may be that the second barrier 450 is advanced with a plunger 430 instead of the inserter tubes 70, 80. After the second barrier 450 is positioned the plunger 430 is removed and the connection member 440 may be exposed on the proximal end of the second barrier 450. The connection member 440 may comprise the same or similar elements as previously depicted and described in FIGS. 8-10. Stops, or notches on the connection member 440 may interact with the collar on the second barrier 450 allowing only a one way advancement of the second barrier 450. After the plunger 430 is removed the connection member 440 may be cut to an appropriate length.

The umbrella like expandable barrier 420 may comprise mesh which may be made of suture-like materials that could be either bio-absorbable or non-absorbable. The materials used for the repair expandable barrier 420 may also be comprised of, or have the consistency of dura mater, and may be even stiffer than dura mater. The mesh-like material may have multiple layers and may also be combined with an expansile hyrdogel polymer which can provide additional filling of the defect and act as a barrier to protect against further CSF leak. The expansile hydrogel polymer may expand once the positioning of the expandable barrier 420 was finalized and the hydrogel polymer is exposed to water or other bodily fluids. The device may be further secured in place with the use of fibrin glue as previously described.

Figure 25:
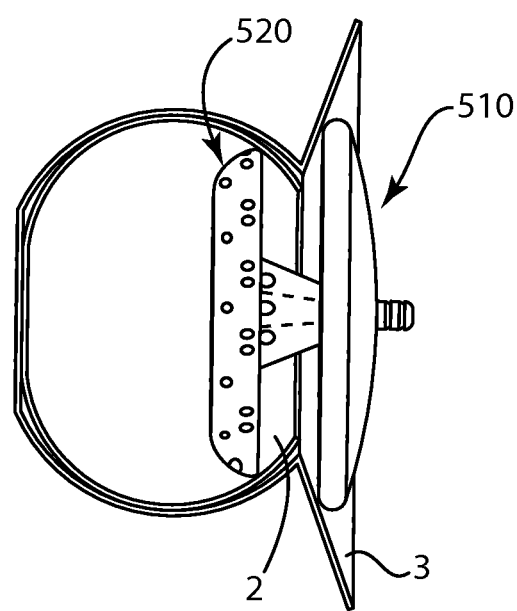
FIG. 25 illustrates a side view, with the defect in cross section, of an alternate embodiment of the device of FIG. 18 with an upside down umbrella inlay, an overlay, and a connection member.

Referring to FIG. 25, a repair device 510 may comprise an expandable barrier 520 which may expand like an umbrella but opposite the direction of the expandable barrier 420 depicted and described in FIGS. 21-25. The remaining structure and function of the repair device 510 may mirror that of the previous embodiment repair device 410. In one embodiment, an umbrella-like expandable barrier 520 may comprise multiple layers, with a non-fenestrated layer, and a fenestrated proximal layer. Fibrin glue may be introduced between the layers with the result that the glue can move proximally through the fenestrated proximal layer into the repair device void between the barriers, but the glue cannot move through the non-fenestrated distal layer, distal to the barrier 520.

Figure 26:
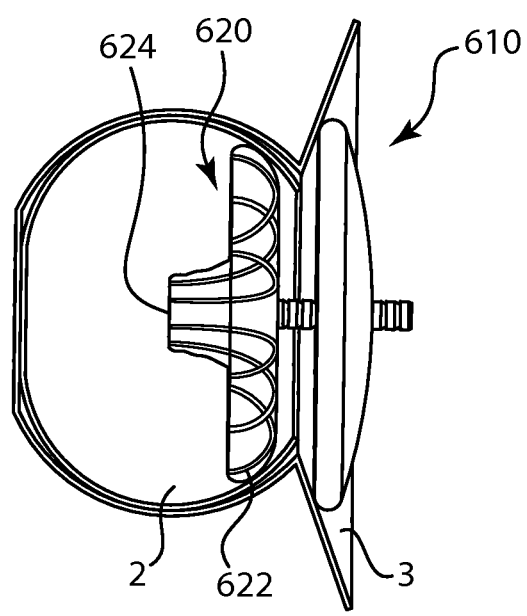
FIG. 26 illustrates a side view, with the defect in cross section, of an alternate embodiment of the device of FIG. 18 with an umbrella inlay with struts, an overlay, and a connection member.

FIG. 26 depicts a repair device 610 with an expandable barrier 620 which is similar to the previous embodiment of the expandable barrier 420 depicted and described in FIGS. 21-25. However, the expandable barrier 620 may also comprise reinforcing limbs 622 extending from the distal end 624 of expandable barrier 620 along the length of the expandable barrier 620 to the periphery of the expanded barrier 620 which engages the inner surface 2 of the defect.

Another alternative embodiment (not shown) may include an expandable barrier which may comprise passive expansion. This embodiment may be a carpet-like device and may comprised of a type of graft material including autologous fascia lata as well as cadaveric or synthetic dural substitutes. The repair device allows the material to be rolled and shaped such that it could be delivered through the defect opening into the defect interior space. During delivery, the repair device may have a collapsed configuration. Once the repair device is in place the collapsed material passively opens or "unrolls" to an expanded configuration in order to obliterate the defect. A passively expandable barrier may also be deployed as an overlay outside the defect opening.

Each of the embodiments presented herein may be used as a single component, as an inlay or overlay or both. Alternatively each of the embodiments presented herein may be used with a second component, for example those embodiments depicted and described in FIGS. 1B, 8, 11 and 24.

The present invention may be embodied in other specific forms without departing from its spirit or essential characteristics. For example, above are described various alternative examples of repair devices with expandable barriers, inlays and overlays as well as different instruments. It is appreciated that various features of the above-described examples can be mixed and matched to form a variety of other combinations and alternatives. It is also appreciated that this system should not be limited simply to CSF leak prevention and repair. This system may also be used to obliterate other defects in soft or hard tissues or to stop other fluid leaks elsewhere in the body.

As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A device for treating a defect, the defect having an inner surface, an outer surface, and a defect opening communicating with the inner surface and the outer surface, the defect opening having a lateral dimension, the device comprising:
   a first compliant, expandable barrier insertable through the defect opening, the first barrier positionable to contact the inner surface and extend across the defect opening to completely cover the defect opening from the inside of the defect;
   a second compliant, expandable barrier positionable to contact the outer surface and extend across the defect opening to completely cover the defect opening from the outside of the defect; and
   a connecting member attached to the first barrier and the second barrier to couple the first barrier to the second barrier in a plurality of lockable positions along a longitudinal axis of the connecting member;
   wherein the first compliant, expandable barrier is a balloon comprising:
      a proximal portion;
      a distal portion;
      a middle portion intermediate the proximal portion and the distal portion;
      a first material; and
      a second material;
   wherein the first material is compliant and the second material is more rigid than the first material, the middle portion of the balloon comprises the first material and the distal portion of the balloon comprises the second material, wherein the first material expands at a greater rate than the second material, such that the lateral expansion of the balloon is greater than the distal expansion of the balloon.

2. The device of claim 1, wherein the balloon is selectively inflatable and deflatable.

3. The device of claim 2, wherein the balloon comprises a first zone and a second zone, wherein the compliance of the first zone varies from the compliance of the second zone such that an extent of expansion of the balloon varies from the first zone to the second zone.

4. The device of claim 1, wherein the first barrier is radially symmetrical, the first barrier comprising an expanded outer diameter, the expanded outer diameter greater than the defect opening lateral dimension.

5. The device of claim 1, further comprising:
   a sealing material, wherein the sealing material is insertable into the defect to secure the device to the defect and prevent movement of fluid into or out of the defect.

6. The device of claim 1, further comprising:
   a reinforcing body, the reinforcing body deployable within the first barrier to provide structural support to the first barrier and prevent unintended retraction of the first barrier.

7. The device of claim 6, wherein the reinforcing body comprises a wire ring.

8. The device of claim 1, wherein the second barrier is slidable relative to the connecting member along the longitudinal axis toward or away from the first barrier.

9. The device of claim 8, wherein the connecting member further comprises a plurality of stops distributed longitudinally along the connecting member; and wherein the second barrier further comprises a collar configured to engage at least one stop, of the plurality of stops, to lock the position of the second barrier relative to the connecting member.

10. A device for treating a defect, the defect having an inner surface, an outer surface, a defect interior space, and a defect opening communicating with the inner surface and the outer surface, the defect opening having a lateral dimension, the device comprising:
- a first balloon having a longitudinal axis, the first balloon comprising an elastomeric member, the first balloon insertable through the defect opening, the first balloon selectively inflatable and deflatable;
- a connecting member coupled to the first balloon, wherein the connecting member defines a longitudinal axis and a tubular bore, wherein the connecting member comprises a plurality of stops distributed peripherally and longitudinally along the connecting member; and
- wherein when the first balloon is inserted through the defect opening and inflated, the first balloon comprises a first expanded configuration having a diameter greater than the defect opening lateral dimension, to completely cover the defect opening from the inside of the defect and prevent movement of fluid through the defect opening;
- wherein the first balloon comprises:
  - a proximal portion;
  - a distal portion;
  - a middle portion intermediate the proximal portion and the distal portion;
  - a first material; and
  - a second material;
- wherein the first material is compliant and the second material is more rigid than the first material, and wherein the middle portion of the first balloon comprises the first material and the distal portion of the first balloon comprises the second material.

11. The device of claim 10, wherein radial expansion of the first balloon relative to the longitudinal axis is greater than the axial expansion of the first balloon relative to the longitudinal axis.

12. The device of claim 10, the first balloon further comprising:
- a first portion;
- a second portion; and
- a neck portion, wherein the first portion is connected to the second portion through the neck portion, the neck portion intermediate the first portion and the second portion;
- wherein the first portion is configured to expand to a first expanded configuration having a diameter greater than the defect opening lateral dimension, to completely cover the defect opening from the inside of the defect and prevent movement of fluid through the defect opening;
- and wherein the second portion is configured to expand to a second expanded configuration having a diameter greater than the defect opening, to completely cover the defect opening from the outside of the defect interior space.

13. The device of claim 10, further comprising:
- a second balloon coupled to the connecting member, the second balloon comprising an elastomeric member, the second balloon selectively inflatable and deflatable, the second balloon comprising a second expanded configuration having a diameter greater than the defect opening lateral dimension, to completely cover the defect opening from the outside of the cavity.

14. The device of claim 13, wherein the bore is in communication with an interior space of the first balloon.

* * * * *